(12) United States Patent
Sturrock et al.

(10) Patent No.: US 7,981,922 B2
(45) Date of Patent: Jul. 19, 2011

(54) ANGIOTENSIN I-CONVERTING ENZYME (ACE) INHIBITORS

(75) Inventors: Edward Sturrock, Cape Town (ZA); Aloysius Nchinda, Cape Town (ZA); Kelly Chibale, Claremont (ZA)

(73) Assignee: University of Cape Town, Cape Town (ZA)

( * ) Notice: Subject to any disclaimer, the term of this patent is extended or adjusted under 35 U.S.C. 154(b) by 881 days.

(21) Appl. No.: 11/921,092

(22) PCT Filed: May 29, 2006

(86) PCT No.: PCT/IB2006/001411
§ 371 (c)(1),
(2), (4) Date: Nov. 27, 2007

(87) PCT Pub. No.: WO2006/126087
PCT Pub. Date: Nov. 30, 2006

(65) Prior Publication Data
US 2009/0118351 A1 May 7, 2009

(30) Foreign Application Priority Data
May 27, 2005 (ZA) .................................. 2005/04365

(51) Int. Cl.
*A61K 31/40* (2006.01)
(52) U.S. Cl. ...................................................... 514/416
(58) Field of Classification Search ................... 514/416
See application file for complete search history.

(56) References Cited

U.S. PATENT DOCUMENTS

| 4,356,118 A | 10/1982 | Owens |
| 4,374,829 A | 2/1983 | Harris et al. |
| 5,008,273 A | 4/1991 | Schnorrenberg et al. |

FOREIGN PATENT DOCUMENTS
WO    WO 2004/087743 A2    10/2004

OTHER PUBLICATIONS

Almquist, R. et al., "Derivatives of the potent angiotensin converting enzyme inhibitor 5(S)-benzamido-4-oxo-6-phenylhexanoyl-L-proline: effect of changes at positions 2 and 5 of the hexanoic acid portion," J. Med. Chem., 1982, 25:1292-1299.
Almquist, R. et al., "Synthesis and biological activity of a ketomethylene analog of a tripeptide inhibitor of angiotensin converting enzyme," J. Med. Chem., 1980, 23:1392-1398.
Antonios, T. et al., "Angiotensin converting enzyme inhibitors in hypertension: potential problems," J. Hypertens, 1995, 13(Suppl 3): S11-S16.
Bala, M. et al., "Novel Peptidomimics as Angiotensin-Converting Enzyme Inhibitors: A Combinatorial Approach," Bioorganic & Medicinal Chemistry, 2002, 10:3685-3691.
Borghi, C. et al., "Double-blind comparison between zofenopril and lisinopril in patients with acute myocardial infarction: Results of the Survival of Myocardial Infarction Long-Term Evaluation-2 (SMILE-2) study," Am. Heart J., 2003, 145:80-87.
Brown, N. et al., "Angiotensin-Converting Enzyme Inhibitors," Circulation, 1998, 97:1411-1420.
Cushman, D. et al., "Design of potent competitive inhibitors of angiotensin-converting enzyme. Carboxyalkanoyl and mercaptoalkanoyl amino acids," Biochemistry, 1977, 16:5484-5491.
Deddish, P. et al., "N-Domain-Specific Substrate and C-Domain Inhibitors of Angiotensin-Converting Enzyme: Angiotensin-(1-7) and Keto-ACE," Hypertension, 1998, 31:912-917.
Georgiadis, D. et al., "Structural Determinants of RXPA380, a Potent and Highly Selective Inhibitor of the Angiotensin-Converting Enzyme C-Domain," Biochemistry, 2004, 43:8048-8054.
Hvidt, T. et al., "Synthesis of enantiomerically pure β-amino-α-methylene-γ-butyrolactones by way of ozonolysis of aromatic α-amino acids," Can. J. Chem., 1988, 66:779-782.
Israili, Z. et al., "Cough and Angioneurotic Edema Associated with Angiotensin-converting Enzyme Inhibitor Therapy: A Review of the Literature and Pathophysiology," Annals of Internal Medicine, 1992, 117:234-242.
Natesh, R. et al., "Crystal structure of the human angiotensin-converting enzyme-lisinopril complex," Nature, 2003, 421:551-554.
Natesh, R.. et al., "Structural Details on the Binding of Antihypertensive Drugs Captopril and Enalaprilat to Human Testicular Angiotensin I-Converting Enzyme," Biochemistry, 2004, 43:8718-8724.
Ondetti, M. et al., "Design of Specific Inhibitors of Angiotensin-Converting Enzyme: New Class of Orally Active Antihypertensive Agents," Science, 1977, 196:441-444.
Peng, S. et al., "Enantiomerically Pure Indoloquinolizines from Tryptophane," Liebigs Ann. Chem., 1990, 313-318.
Raia, Jr. J. et al., "Angiotensin-Converting Enzyme Inhibitors: A Comparative Review," DICP Ann. Pharmacother., 1990, 24:506-525.
Soubrier, F. et al., "Two putative active centers in human angiotensin I-converting enzyme revealed by molecular cloning," Proc. Natl. Acad. Sci. USA., 1988, 85:9386-9390.
Peach, M., "Renin-Angiotensin System: Biochemistry and Mechanisms of Action," Physiol. Rev., 1977, 57:313-370.
Ehlers, M. et al., "Angiotensin-Converting Enzyme: New Concepts Concerning Its Biological Role," Biochemistry, 1989, 28:5311-5318.
Meyer, R. et al., "Novel Synthesis of (S)-1[5-(Benzoylamino)-1,4-dioxo-6-phenylhexyl]-L-proline and Analogues: Potent Angiotensin Converting Enzyme Inhibitors," J. Med. Chem., 1981, 24:964-969.
Gonzalez-Muniz, R. et al., "Ketomethylene and (Cyanomethylene)amino Pseudopeptide Analogues of the C-Terminal Hexapeptide of Neurotensin," J. Med. Chem., 1995, 38:1015-1021.
Garcia-Lopez, M.T. et al., "A Simple and Versatile Route to Ketomethylene Dipeptide Analogs," Tetrahedron Letters, 1988, 29:1577-1580.
Garcia-Lopez, M.T. et al., "Synthesis of Ketomethylene Dipetides Containing Basic Amino Acid Analogues at C-Terminus," Tetradron, 1988, 44:5131-5138.
Kelly, T.R. et al., "A Convenient Preparation of Methyl and Ethyl Gloyoxylate," Synthesis, 1972, 544-545.
Accelyrs-Additional Products, available at http://accelrys.com/products/additional-products.html printed as of Oct. 16, 2009.

(Continued)

*Primary Examiner* — San-ming Hui
(74) *Attorney, Agent, or Firm* — Kilpatrick Townsend & Stockton LLP

(57) ABSTRACT

This invention relates to a process for synthesizing an amino acid derivative of a tripeptidomimetic, such as lisinopril. The invention also relates to a derivative of lisinopril, incorporating a amino acid moeity such as tryptophan at the P2' position.

3 Claims, No Drawings

OTHER PUBLICATIONS

Benedetti, F. et al., "Versatile and Stereoselective Synthesis of Diamino Diol Dipeptide Isosteres, Core Units of Pseudopeptide HIV Protease Inhibitors," J. Org. Chem., 1997, 62:9348-9353.

Benedetti, F. et al., "Stereoselective Synthesis of Non Symmetric Dihydroxyethylene Dipeptide Isosteres Via Epoxyalcohols Derived From α-Amino Acids," Bioorganic & Medicinal Chemistry Letters, 1999, 9:3027-3030.

Benedetti, F. et al., "New synthesis of 5-amino-4-hydroxy-2,6-dimethylheptanoic acid, a hydroxyethylene isostere of the Val-Ala dipeptide," Tetrahedron Letters, 2000, 41:10075-10078.

Bersanetti, P. et al., "Positional-Scanning Combinatorial Libraries of Fluorescence Resonance Energy Transfer Peptides for Defining Substrate Specificity of the Angiotensin I-Converting Enzyme and Development of Selective C-Domain Substrates," Biochemistry, 2004, 43:15729-15736.

Buikema, H., "Angiotensin-converting enzyme inhibitors zofenopril and lisinopril are both safe in the treatment of acute myocardial infarction," Evidence-based Cardiovascular Medicine, 2003, 7:131-132.

Da, C. et al., "A convenient synthesis of piperidine-based β-amino alcohols from L-Phe and highly enantioselective addition of diethyl zinc to aldehydes," Tetrahedron: Asymmetry, 2003, 14:659-665.

Deziel, R. et al., "A Practical and Diastereoselective Synthesis of Ketomethylene Dipeptide Isosteres of the Type AAψ[COCH$_2$]Asp," J. Org. Chem., 1996, 61:2901-2903.

Erdos, E., "Conversion of Angiotensin I to Angiotensin II," Am. J. Med., 1976, 60:749-759.

Ghosh, A. et al., "Transition-State Mimetics for HIV Protease Inhibitors: Stereocontrolled Synthesis of Hydroxyethylene and Hydroxyethylamine Isosteres by Ester-Derived Titanium Enolate Syn and Anti-Aldol Reactions," J. Org. Chem., 1998, 63:6146-6152.

Nchinda, A. et al., "Synthesis and molecular modeling of a lisinopril-tryptophan analogue inhibitor of angiotensin I-converting enzyme," Biorganic & Medicinal Chemistry Letters, 2006, 16:4616-4619.

Skeggs, L. et al., "The Preparation and Function of the Hypertensin-Converting Enzyme," J. Exp. Med., 1956, 103:295-299.

Tossi, A. et al., "Small hydroxyethylene-based peptidomimetics inhibiting both HIV-1 and C. albicans aspartic proteases," Bioorganic & Medicinal Chemistry, 2003, 11:4719-4727.

International Search Report mailed Dec. 12, 2006 corresponding to Application No. PCT/IB2006/001411.

Written Opinion of the International Searching Authority mailed Dec. 19, 2007 corresponding to Application No. PCT/IB2006/001411.

ANGIOTENSIN I-CONVERTING ENZYME (ACE) INHIBITORS

BACKGROUND OF THE INVENTION

Angiotensin I-converting enzyme (ACE; EC 3.4.15.1) is a zinc-dipeptidyl carboxypeptidase that plays a key role in blood pressure regulation by converting the inactive decapeptide angiotensin I to the potent vasopressor octapeptide angiotensin II by cleavage of the carboxy-terminal dipeptide.[1] It also inactivates the vasodepressor nonapeptide bradykinin.[2,3] Thus, the inhibition of ACE has become a primary strategy in the treatment of hypertension, myocardical infarction, heart failure, and diabetic nephropathy.[4] There are a number of commercially available ACE inhibitors, including captopril,[5,6] lisinopril, and enalapril, which have established themselves in the therapy of hypertension and congestive heart failure.[7,8] However, undesirable side effects such as persistent cough, loss of taste, and angioedema have been associated with current-generation ACE inhibitors.[9,10] Therefore, the development of novel effective drugs for the treatment of hypertension and cardiovascular diseases still remains an important goal. The recent availability of the crystal structure of the testis ACE-lisinopril complex has opened the possibility of structure-guided design of second-generation, domain-selective ACE inhibitors.[11]

SUMMARY OF THE INVENTION

According to a first embodiment of the invention, there is provided a process for synthesising an amino acid derivative of a tripeptidomimetic, such as a tryptophan derivative of lisinopril, the process including the steps of:
peptide coupling a dipeptide, typically a carboxyl dipeptide, with a methyl ester having an amino moeity, typically a L-tryptophan methyl ester, to produce a dipeptide methyl ester; and
hydrolysing the dipeptide methyl ester to produce the tripeptidomimetic.

The dipeptide is preferably coupled to the $P_2'$ residue of the dipeptide methyl ester.

The carboxyl dipeptide may be that of lisinopril, enalaprilat, perindoprilat, cilazaprilat etc.

The dipeptide may be produced by reductively aminating a butyrate such as 2-oxo-aryl butyrate, typically ethyl 2-oxo-4-phenyl butyrate and a tert-butoxycarbonyl-L-amino acid such as N-ε-(tert-butoxycarbonyl)-L-lysine.

The dipeptide methyl ester is preferably an amino methyl ester such as tryptophan or phenylalanine methyl ester.

According to a second embodiment of the invention, there is provided a compound produced by the process described above.

According to a third embodiment of the invention, there is provided a tripetidomemetic, preferably a derivative of lisinopril, incorporating a amino acid moeity, preferably tryptophan, at the $P_2'$ position.

The tryptophan derivative of lisinopril may be N—[$N^6$-tert-butoxycarbonyl-L-lysyl-$N^2$—(R,S)-(1-ethoxycarbonyl-3-phenylpropyl)]-L-tryptophan methyl ester or $N^2$—(R,S)-(1-Carbonyl-3-phenylpropyl)]-L-lysyl-L-tryptophan hydrochloride.

According to a fourth embodiment of the invention, there is provided a pharmaceutical composition including a compound described above. The compound may be for the treatment of hypertension and/or cardiovascular disease.

DETAILED DESCRIPTION OF THE INVENTION

The synthesis of lisinopril incorporating a tryptophan moiety at the $P_2'$ position is described herein.

ACE is a complex two-domain enzyme, comprising an N and a C domain, each containing an active site with similar but distinct substrate specificities and chloride-activation requirements. The N- and C-domain sites of ACE hydrolyze angiotensin 1 (Ang I) and bradykinin (BK) at comparable rates in vitro, but in vivo it appears that the C-domain is primarily responsible for regulating blood pressure. This might suggest that a C-selective inhibitor would have a profile comparable to current mixed inhibitors, but this is not necessarily the case.

First, while Ang I is hydrolyzed predominantly by the C domain in vivo, BK is hydrolyzed by both domains and therefore selective inhibition of the C-domain site will allow some level of BK degradation to continue, catalyzed by the N-domain. This could be sufficient to prevent the excessive BK accumulation that has been observed during attacks of angioedema. Second, BK potentiation by $B_2$ receptor resensitization is maximal when both the N- and C-domains are inhibited, suggesting that a pure C-selective inhibitor will have a lower propensity for excessive BK stimulation. Third, the multiple Ang and non-Ang peptides known to be vasoactive are not hydrolyzed equally by the two domains, making it likely that the ratio of vasopressor to vasodilator peptides will differ between C-selective and mixed inhibitors. Thus, a highly selective C-domain inhibitor has the potential for effective blood pressure control with reduced vasodilator-related side effects.

In contrast to a C-selective inhibitor, an N-selective inhibitor may open up novel therapeutic areas. As discussed, the N-domain appears to play a minor role in blood pressure control in vivo. At least three physiologically important peptides are hydrolyzed preferentially or exclusively by the N domain: luteinizing hormone-releasing hormone (LH-RH), Ang$_{(1-7)}$, and AcSDKP (N-acetyl-seryl-aspartyl-lysyl-proline). The contribution of ACE to the metabolism of LH-RH and Ang$_{(1-7)}$ in vivo is unclear, but there is increasing evidence that ACE is the principal metabolizing enzyme for AcSDKP, a natural hemoregulatory hormone. AcSDKP has anti-proliferative and anti-fibrotic activities and may have utility in protecting hematopoietic stem cells against chemotherapy-induced injury and in limiting cardiac fibrosis. Administration of ACE inhibitors results in a 4-6-fold elevation of AcSDKP plasma levels. This may be the basis for the observed association between ACE inhibitors and anemia, and the effective treatment of altitude polycythemia by the ACE inhibitor enalaprilat.

Lisinopril, which is a commercially available ACE inhibitor, is active with a nanomolar inhibition constant and has been shown to be relatively safe and effective for the treatment of patients with acute myocardial infarction,[32] hypertension, and heart-related diseases.[33-35]

Lisinopril is chemically described as (S)-1-[$N^2$-(1-carboxy-3-phenylpropyl)-L-lysyl]-L-proline dihydrate. Its empirical formula is $C_{21}H_{31}N_3O_5.2H_2O$ and its structural formula is:

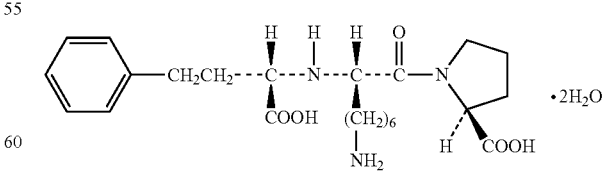

Dive and co-workers[36] have recently reported that a phosphinic ACE-inhibitor, RXP A380, is ~3000-fold C-domain selective and these same researchers have further shown that one key feature of the C-domain selectivity is the tryptophan moiety at the $P_2'$ position.

Starting material 3 was prepared by the reductive amination of ethyl 2-oxo-4-phenyl butyrate 1 and N-ε-(tert-butoxycarbonyl)-L-lysine 2 using an ethanolic solution of NaBH$_3$CN.[37] The ratio of the two diastereoisomers was observed as 60:40 from the $^1$H NMR spectrum. Peptide coupling of compound 3 with a L-tryptophan methyl ester 4 (prepared earlier by methylation of tryptophan in the presence of thionyl chloride and methanol according to the method described by Hvidt et al.[38]) was effected using EDC.HCl in the presence of HOBt and diisopropyl ethyl amine as a base to afford the diastereomeric pseudopeptide 5 in 74% yield. The characterisation of this diastereomeric mixture was achieved from the EI-MS and spectroscopic data. The EI-MS data indicated a molecular ion peak at 637 corresponding to M$^+$+H. The $^1$H NMR spectrum showed two singlets at δ 3.71 and 3.73 ppm corresponding to the two methoxy groups of the diastereomeric mixture 5. Acid hydrolysis of the resulting diastereomeric mixture 5 produced the hydrochloride salt of the diastereomeric mixture 6 in a quantitative yield. Evidence of the compound 6 was found from the disappearance of the Boc, methyl and ethyl signals on the $^1$H NMR spectrum. Purification and separation of the diastereomeric mixture 6 was done by HPLC.

Initial attempts to remove the Boc group with concomitent hydrolysis of the ethyl and methyl esters under acid conditions afforded a mixture of four products separated by HPLC. These four products $P_1$, $P_2$, $P_3$ and $P_4$ were generated as a result of incomplete hydrolysis of compound 5, since acid hydrolysis of ester at room temperature is relatively slow. The EI-MS data revealed molecular ion peaks at 522, 522, 536 and 536 for $P_1$, $P_2$, $P_3$ and $P_4$, respectively. However, the diastereomeric mixture 5 was stirred in 4N HCl at room temperature for 24 h, after which the solvent was evaporated and the mixture was then stirred with a solution of 0.5N LiOH for a further 5 h to afford the desired product 6. The characterisation of this diastereomeric mixture 6 was achieved from the EI-MS and spectroscopic data that gave a molecular ion peak at 495 corresponding to M$^+$+H. Purification and separation of the diastereomeric mixture 6 by HPLC gave the required two diastereoisomers in a 60:40 ratio.

ACE inhibition assays were carried out on the incomplete hydrolysis products $P_1$, $P_2$, $P_3$ and $P_4$.

Incomplete hydrolysis products

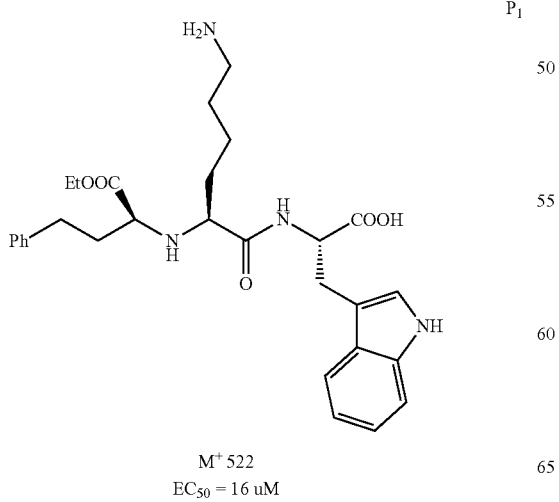

$P_1$

M$^+$ 522
EC$_{50}$ = 16 uM

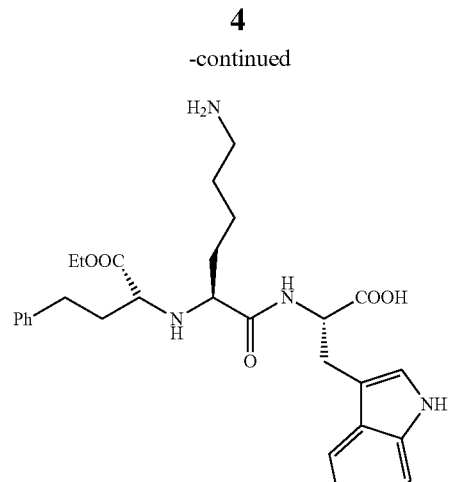

$P_2$

M$^+$ 522
EC$_{50}$ = 419 uM

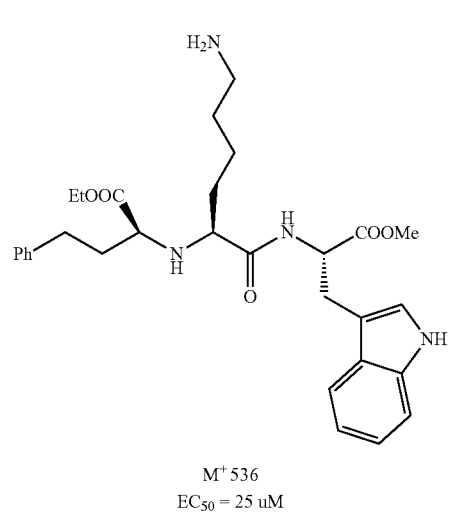

$P_3$

M$^+$ 536
EC$_{50}$ = 25 uM

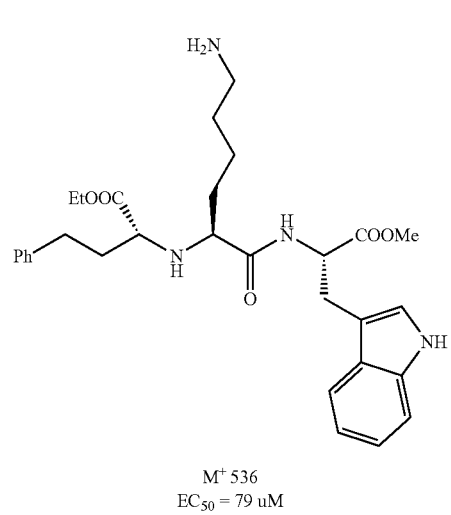

$P_4$

M$^+$ 536
EC$_{50}$ = 79 uM

Scheme

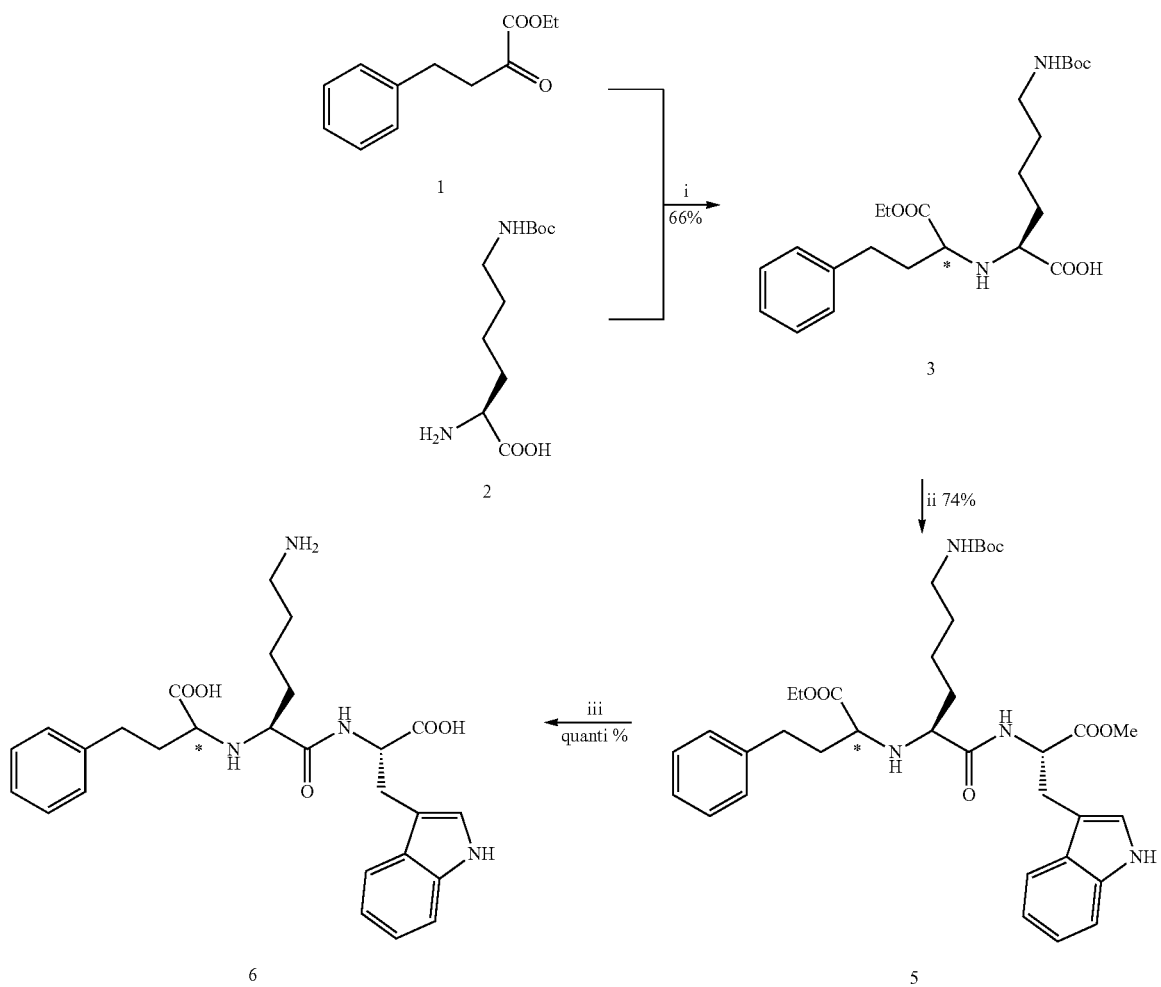

Reagents and Conditions:
(i) ketone 1 (4.0 eq), amino acid 2 (1.0 eq), NaBH$_3$CN (2.0 eq), 50% EtOH/H$_2$O, rt, 12 h; (ii) L-tryptophan methyl ester 4, EDC.HCl, HOBt, iPr$_2$NEt (1.0 equiv), dry DMF, rt, 72 h; (iii) (a) 4N HCl, EtOAc, rt, 24 h; (b)) 0.5N LiOH, THF-MeOH, rt, 5 h.

It will be apparent to a person skilled in the art that it will also be possible to synthesize other compounds than those described above by the method of the invention. Lisinopril is a carboxyalkyl dipeptide, essentially a Phe-Lys-Pro analog. Compound 6 is a tryptophan derivative of lisinopril—i.e. the Pro in the P2' position has been substituted by a Trp. It should be possible to prepare numerous variations on this theme, with different Trp-like groups in the P2' position. Also, the Zn-binding carboxyl could be changed to a keto group or any one of the possibilities mentioned above.

Similarly, the functionalities in the P1' and P1 position could be changed. In particular, the crystal structure indicates that the S1' pocket can accommodate larger side chains, and the applicant is in the process of studying a lisinopril analog with an arginine (or arginine-like) residue replacing the lysine in the P1' position.

The invention will now be described in more detail with reference to the following non-limiting examples.

EXAMPLES

General Procedure

All reactions were carried out under a nitrogen atmosphere, unless otherwise specified. Reactions were monitored by TLC using Merck 60 F$_{254}$ precoated silica gel plates. Detection was effected by observation under a UV lamp (wavelength of 254 nm) and developed with I$_2$. Column chromatography was carried out on silica gel and the eluent mixture used is specified in each experiment. Anhydrous solvents like dichloromethane were distilled from phosphorous pentoxide and stored over molecular sieves type 4 Å. All other anhydrous solvents were obtained from Aldrich or Sigma or Merck Chemical Co. All melting points were determined using a Kofler hot plate apparatus and are uncorrected. Specific rotations ([α]$_D$) were measured at 20° C., unless otherwise specified, using a Perkin-Elmer 141 polarimeter and are recorded in units of $10^{-1}$ ° cm$^2$ g$^{-1}$. NMR spectra were obtained on a Varian Mercury 300 MHz or Varian Unity 400 MHz spectrometer. Chemical shifts are reported in ppm relative to the residual signal of the solvent used. The coupling constants, where specified, are given in hertz (Hz). Mass spectra were obtained using electron impact ionization.

Example 1

N—[N⁶-tert-butoxycarbonyl-L-lysl-N²—(R,S)-(1-ethoxycarbonyl-3-phenylpropyl)]-L-tryptophan Methyl Ester 5

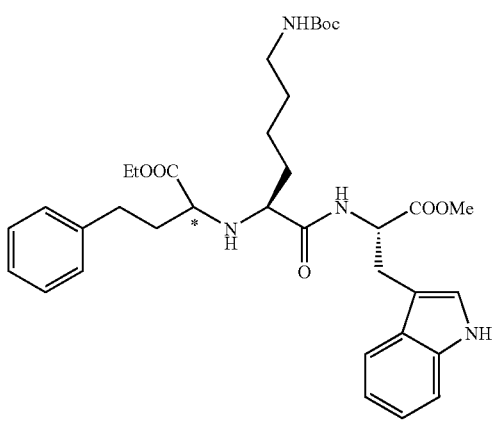

(NACE 99)

A solution of N—[N⁶-tert-butoxycarbonyl-N²—(R,S)-(1-ethoxycarbonyl-3-phenylpropyl)]-L-lysine 3 (200 mg, 0.459 mmol, 1.0 eq.) and L-tryptophan methyl ester 4 (100 mg, 0.459 mmol, 1.0 eq.) in dry DMF (10 mL) was cooled at 0° C. 1-Hydroxybenzotriazole hydrate (HOBt) (62 mg, 0.459 mmol, 1.0 eq.), N-ethyl-N'-(dimethylaminopropyl)-carbodiimide hydrochloride (EDC.HCl) (88 mg, 0.459 mmol, 1.0 eq.) and iPr₂NEt (0.079 mL, 0.459 mmol, 1.0 eq.) were added and the resulting mixture stirred at 0° C. for 2 h. The cooling bath was removed and the reaction mixture then stirred for a further 72 h at room temperature. The reaction mixture was diluted with H₂O (30 mL) and the extracted with EtOAc (3×30 mL). The combined organic extract were washed sequentially with saturated aqueous NaHCO₃ (30 mL), brine (30 mL), and dried over anhydrous MgSO₄. Evaporation of the solvent gave a crude residue, which was subjected to column chromatography on silica gel elution with 66% EtOAc-hexane afforded the desired diastereomeric mixture N—[N⁶-tert-butoxycarbonyl-L-lysyl-N²—(R,S)-(1-ethoxycarbonyl-3-phenylpropyl)]-L-tryptophan methyl ester 5 as a pale yellow oil (0.215 g, 74%); $R_f$ 0.27 (66% EtOAc-hexane); IR (liquid film) v 1718 (CO), 3300 (NH) cm⁻¹; ¹H NMR (300 MHz, CDCl₃), duplication of the signals are due to the diastereomeric mixture, $\delta_H$ 1.23 (3H, t, J=7.1 Hz, —OCH₂CH₃), 1.25 (3H, t, J=7.2 Hz, —OCH₂CH₃), 1.47 (9H, s, (CH₃)₃), 1.48 (9H, s, (CH₃)₃), 1.52-1.87 (12H, m, 6×-CH₂), 1.91-2.21 (4H, m, 2×-CH₂), 2.49 (2H, m, —CH₂Ph), 2.58 (2H, t, J=7.2 Hz, —CH₂Ph), 2.91-3.11 (4H, m), 3.12-3.45 (2H, m), 3.71 (3H, s, OCH₃), 3.73 (3H, s, OCH₃), 4.12 (2H, q, J=7.2 Hz, —OCH₂CH₃), 4.13 (2H, q, J=7.0, —OCH₂CH₃), 4.14 (2H, m, 2×-CH—), 4.58 (2H, br s, 2×—NH), 4.89 (1H, m, —CH—), 4.95 (1H, m, —CH—), 6.97-7.48 (26H, m, Ar—H), 7.55 (1H, t, J=8.4 Hz,), 7.56 (1H, t, J=8.4 Hz,), 8.69 (1H, br s, —NH-pyrrole) and 8.87 (1H, br s, —NH-pyrrole); ¹³C NMR (75 MHz, CDCl₃) $\delta_C$ 14.2, 21.0, 22.2, 22.5, 27.6, 27.7, 28.5, 30.0, 31.7, 32.0, 32.7, 33.6, 35.5, 40.3, 51.8, 52.3, 58.8, 60.2, 60.4, 61.0, 62.0, 111.3, 111.4, 118.5, 119.4, 119.5, 122.0, 122.1, 122.9, 126.0, 126.1, 127.6, 128.3, 128.4, 128.5, 136.2, 136.3, 141.0, 141.6, 156.2, 156.3, 162.53, 171.1, 172.4, 173.6 and 174.96; EI-MS m/z 637 (M⁺+H).

Example 2

N²—(R,S)-(1-Carbonyl-3-phenylpronyl)]-L-lysyl-L-tryptophan hydrochloride

Incomplete Hydrolysis Products P₁, P₂, P₃ and P₄

To a solution of the diastereomeric mixture N—[N⁶-tert-butoxycarbonyl-L-lysyl-N²—(R,S)-(1-ethoxycarbon-yl-3-phenylpropyl)]-L-tryptophan methyl ester 5 (100 mg, 0.157 mmol) in EtOAc (5.0 mL) was added 4N HCl (10 mL) and the resulting mixture was stirred at room temperature for 2 h. TLC showed the disappearance of the starting material. Evaporation of the solvent after neutralization with 2N NaOH gave incomplete hydrolysis products P₁, P₂, P₃ and P₄ as a cream white solid material in quantitative yield; IR (liquid film) v 1720 (CO), 2980 (OH) and 3115 (NH) cm⁻¹. The EI-MS data of indicated a molecular ion peaks at 522, 522, 536 and 536 for P₁, P₂, P₃ and P₄ respectively.

Example 3

N²—(R,S)-(1-Carbonyl-3-phenylpropyl) 1-L-lysyl-L-tryptophan Hydrochloride 6

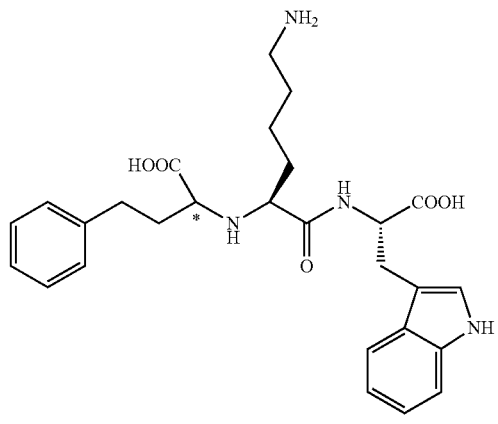

(NACE 102F)

To a solution of the diastereomeric mixture N—[N⁶-tert-butoxycarbonyl-L-lysyl-N²—(R,S)-(1-ethoxycarbon-yl-3-phenylpropyl)]-L-tryptophan methyl ester 5 (50 mg, 0.0785 mmol) in EtOAc (5.0 mL) was added 4N HCl (10 mL) and the resulting mixture was stirred at room temperature for 24 h. Evaporation of the solvent and the residue was dissolved in 0.5N LiOH (5.0 mL) and stirred at room temperature for 5 h. TLC showed the disappearance of the starting material. Evaporation of the solvent after neutralization with 1N HCl gave N²—(R,S)-(1-Carbonyl-3-phenylpropyl)]-L-lysyl-L-tryptophan hydrochloride 6 as a cream white solid material in quantitative yield; IR (liquid film) v 1720 (CO), 2980 (OH) and 3115 (NH) cm⁻¹; IR (KBr) v 1715 (CO) and 3250 (broad, COOH/NH) cm⁻¹; ¹H NMR (400 MHz, D₂O) $\delta_H$ 1.09-1.36 (2H, m, —CH₂CH₂CH₂NH₂), 1.56-1.80 (4H, m, —CH₂CH₂CH₂CH₂NH₂), 2.27 (2H, q, J=7.3 Hz, —CH₂CH₂Ph), 2.34-2.49 (4H, m, —CH₂Ph and —CH₂NH₂), 2.83 (1H, dd, J=6.2 and 13.0 Hz, —CH$_\alpha$Trp), 3.05 (1H, dd, J=6.3 and 13.2 Hz, —CH$_\beta$Trp), 3.31 (2H, m, 2×-CH—), 4.63 (1H, m, —CH—) and 7.01-7.70 (10H, m, Ar—H); ¹³C NMR (100 MHz, D₂O) $\delta_C$ 20.9, 27.3, 30.7, 31.0, 31.4, 33.3, 39.9, 48.6, 55.0, 58.8, 59.5, 62.7, 110.0, 111.5, 118.3, 118.9, 121.5, 123.6, 125.7, 128.2, 128.3 (2C), 126.9, 135.9, 142.1, 142.4, 175.6, 178.5 and 181.0 (duplication of peaks due the two diastereoisomers); EI-MS m/z calcd for $C_{29}H_{34}N_4O_5$ ($M^+$) 494.2429. found 495 ($M^+$+H). HPLC purification and separation give the required two diastereoisomers in a 60:40 ratio.

Example 4

HPLC Purification and Separation

RP-HPLC purification and separation of the incomplete hydrolysis products was performed using a Jupiter 5U C18 300A, size 250×4.60 mm column with gradient elution of t=0 min (63% A, 37% B) and t=30 min (50% A, 50% B); solvent A=0.1% TFA in $H_2O$ and solvent B=0.1% TFA and 75% $CH_3CN$ in $H_2O$; a flow rate of 1.0 mL/min and a 215 and 280 nm UV wavelength detection.

$t_R$=12.77 min for $P_1$, $t_R$=14.5 min for $P_2$, $t_R$=17.1 min for $P_3$ and $t_R$=21.1 min for $P_4$.

RP-HPLC purification and separation of the diastereomeric mixture 4 was performed using a Jupiter 5U C18 300A, size 250×4.60 mm column with gradient elution of t=0 min (50% A, 50% B) and t=50 min (40% A, 60% B); solvent A=0.1% TFA in $H_2O$ and solvent B=0.1% TFA and 75% $CH_3CN$ in $H_2O$; a flow rate of 1.0 mL/min and a 215 and 280 nm UV wavelength detection.

$t_R$=32.1 min for $P_1$ and $t_R$=41.0 min for $P_2$.

Example 5

ACE Inhibitory Activity

The ACE inhibitory activity (as tabulated in Table 1) was measured by the fluorometric determination of pthaldialdehyde-derivatised histidylleucine, a product of the enzyme reaction according to the method of Almquist et al.,[12] with some modifications. For tACEdelta36NJ and N-domain inhibition using Z-Phe-His-Leu as substrate: —10 µL of 0.05 mg/mL enzyme+120 µL inhibitor at ambient temperature for 3 hours. Inhibitor concentrations ranged from 2.0 µM to 500 µM. A 3.0 µL aliquot of this was assayed for enzyme activity using 30 µL of 1.0 mM Hip-His-Leu. This was incubated (in triplicate) for 30 mins at 37° C. and stopped with 180 µL solution of 0.28N NaOH. To this alkalized mixture 12 µL of o-pthaldialdehyde (150 mM) was added and the mixture incubated for another 10 mins at room temperature. Reactions were stopped by adding 26 µL solution of 3N HCl. Fluorescence was measured at Ex=360 nm; Em=486 nm, 5×5 slit width along with a His-Leu standard calibration curve fluorometer: Varian Cary Eclipse plate reader.

All assays included enzyme incubated with buffer in the absence of inhibitor (i.e. 0 µM inhibitor concentration). Lisinopril was also used as a positive control. The 50% inhibition ($IC_{50}$) of ACE activity was calculated as the concentrations of samples that inhibited 50% of ACE activity under these conditions.

TABLE 1

| ACE inhibition of the Phe-Lys-Trp derivatives prepared above | | | |
|---|---|---|---|
| Compound | Structure | $K_i$ (tACE) ZPHL | $K_i$ (N-dom) ZPHL |
| Lisinopril | | 8.03 nM | 367 nM |
| 6 | | 26.3 µM | >500 µM* |

TABLE 1-continued

ACE inhibition of the Phe-Lys-Trp derivatives prepared above

| Compound | Structure | $K_i$ (tACE) ZPHL | $K_i$ (N-dom) ZPHL |
|---|---|---|---|
| 6a | 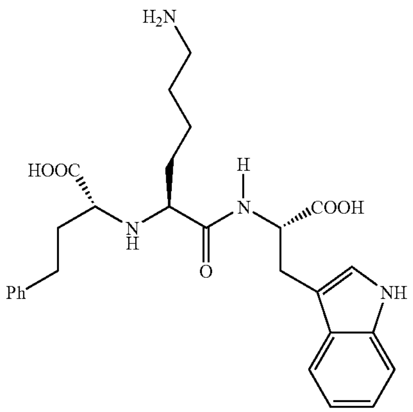 | 7.0 µM | >500 µM* |

Compounds 6 and 6a are two diastereoisomers of a lisinopril derivative incorporating a Trp at the P2' position. Their ACE inhibitory activities are shown in Table 1. Although they displayed Ki values in the low micromolar range, the introduction of a tryptophan moiety at the P2' position resulted in a marked increase in C domain-selectivity (>19->72 fold) as compared with lisinopril (2.6-fold). Neither compound inhibited the N domain up to a concentration of 500 µM (Table 1). Compound 6a, with an S-configuration at the stereogenic centre bearing the zinc-binding carboxylate group, was more C-selective than its R-diastereoisomer (Compound 6).

REFERENCES

1 Skeggs, L. T.; Kahn, J. R. and Shumway, N. P. (1956) The preparation and function of the hypertension-converting enzyme, *J. Exp. Med.* 103, 295-299.
2 Erdös, E. G. (1976) Conversion of angiotensin I to angiotensin II, *Am. J. Med.* 60, 749-759.
3 Peach, M. J. (1977) Renin-angiotensin system: Biochemistry and mechanism of action, *Physiol. Rev.* 57, 313-370.
4 Ehlers, M. R. W and Riordan, J. F. (1989) Angiotensin-converting enzyme: New concepts concerning its biological role, *Biochemistry*, 28, 5312-5318.
5 Cushman, D. W.; Cheung, H. S.; Sbo, E. F. and Ondetti, M. A. (1977) Design of potent competitive inhibitors of angiotensin-converting enzyme. Carboxyalkanoyl and mercaptoalkanoyl amino acids, *Biochemistry*, 16, 5484-5491.
6 Ondetti, M. A.; Rubin, B. and Cushman, D. W. (1977) Design of specific inhibitors of angiotensin-converting enzyme: New class of orally active antihypertensive agents, *Science*, 196, 441-444.
7 Brown, N. J. and Vaughan, D. E. (1998) Angiotensin-converting enzyme inhibitors, *Circulation*, 97(14), 1411-1420.
8 Raia, Jr. J. J.; Barone, J. A.; Byerly, W. G. and Lacy, C. R. (1990) Angiotensin-converting enzyme inhibitors: A comparative review, *DICP*, 24(5), 506-525.
9 Antonios, T. F. and MacGregor, G. A. (1995) Angiotensin-converting enzyme inhibitors in hypertension: Potential problems, *J. Hypertens. Suppl.*, 13(*Suppl*), S11-S16.
10 Israili, Z. H. and Hall, W. D. (1992) Cough and angioneurotic edema associated with angiotensin-converting enzyme inhibitor therapy: A review of the literature and pathophysiology, *Annals in Internal Medicine*, 117, 234-242.
11 Natesh, R.; Schwager, S. L. U.; Sturrock, E. D. and Acharya, K. R. (2003) Crystal structure of the human angiotensin-converting enzyme-lisinopril complex, *Nature*, 421, 551-554.
12 Almquist, R. G.; Chao, W.-R.; Ellis, M. E. and Johnson, H. L. (1980) Synthesis and biological activity of a ketomethylene analogue of a tripeptide inhibitor of angiotensin-converting enzyme, *J. Med. Chem.*, 23, 1392-1398.
13 Meyer, R. F.; Nicolaides, E. D.; Tinney, F. J.; Lunney, E. A.; Holmes, A.; Hoefle, M. L.; Smith, R. D.; Essenburg, A. D.; Kaplan, H. R. and Almquist, R. G. (1981) Novel synthesis of (S)-1-[5-(benzoylamino)-1,4-dioxo-6-phenylhexyl]-L-proline and analogues: Potent angiotensin-converting enzyme inhibitors, *J. Med. Chem.*, 24, 964-969.
14 (a) Almquist, R. G.; Crase, J.; Jennings-White, C.; Meyer, R. F.; Hoefle, M. L.; Smith, R. D.; Essenburg, A. D. and Kaplan, H. R. (1982) Derivatives of the potent angiotensin-converting enzyme inhibitors 5(S)-benzamido-4-oxo-6-phenylhexanoyl-L-proline: Effect of changes at positions 2 and 5 of the hexanoic acid portion, *J. Med. Chem.*, 25, 1292-1299.
(b) Deddish, P. A.; Marcic, B.; Jackmann, H. L.; Wang, H. Z.; Skidgel, R. A. and Erdös, E. G. (1998) N-domain-specific substrate and C-domain inhibitors of angiotensin-converting enzyme: Angiotensin-(1-7) and Keto-ACE, *Hypertension*, 31, 912-917.
15 González-Muñiz, R.; García-López, M. T.; Gómez-Monterrey, I.; Herranz, R.; Jimeno, M. L.; Suárez-Gea, M. L; Johansen, N. L.; Madsen, K.; Thøgersen, H.; and Suzdak, P. (1995) Ketomethylene and (Cyanomethylene) amino pseudopeptide analogues of the C-terminal hexapeptide of neurotensin, *J. Med. Chem.*, 38, 1015-1021 and references cited therein.
16 Dézil, R.; Plante, R.; Caron, V.; Grenier, L.; Llinas-Brunet, M.; Duceppe, J.-S.; Malenfant, E. and Moss, N. (1996) A practical and diastereoselctive synthesis of Ketomethylene dipeptide isosteres of the type AAψ(COCH$_2$)Asp, *J. Org. Chem.*, 61, 2901-2903.
17 Benedetti, F.; Miertus, S.; Norbedo, S.; Tossi, A. and Zlatoidzky, P. (1997) Versatile and stereoselective synthesis of diamino diol dipeptide isosteres: Core units of pseudopeptide HIV protease inhibitors, *J. Org. Chem.*, 62, 9348-9353.
18 Ghosh, A. K. and Fidanze, S. (1998) Transition-state mimetics for HIV protease inhibitors: Stereocontrolled synthesis of hydroxyethylene and hydroxyethylamine isosteres by ester-derived titanium enolate syn and anti-diol reactions, *J. Org. Chem.*, 63, 6146-6152.
19 Benedetti, F.; Maman, P. and Norbedo, S. (2000) New synthesis of 5-amino-4-hydroxy-2,6-dimethylheptanoic acid: A hydroxyethylene isostere of the Val-Ala dipeptide, *Tetrahedron Lett.*, 41, 10075-10078.
20 Benedetti, F.; Magnan, M.; Miertus, S.; Norbedo, S.; Parat, D. and Tossi, A. (1999) Stereoselective synthesis of non symmetric dihydroxyethylene dipeptide isosteres via epoxyalcohols derived from α-amino acids, *Bioorg. Med. Chem. Lett.*, 9, 3027-3030.
21 Tossi, A.; Benedetti, F.; Norbedo, S.; Skrbec, D.; Berti, F. and Romeo, D. (2003) Small hydroxyethylene-based peptidomimetics inhibiting both HIV-1 and *C. albicans* aspartic proteases, *Bioorg. Med. Chem.*, 11, 4719-4727.
22 García-López, M. T.; González-Muñiz, R. and Harto, J. R. (1988) A simple and versatile route to ketomethylene dipeptide analogues, *Tetrahedron Lett.*, 29, 1577-1580.
23 García-López, M. T.; González-Muñiz, R. and Harto, J. R. (1988) Synthesis of ketomethylene dipeptides containing basic amino acid analogues at C-terminus, *Tetrahedron*, 44, 5131-5138.
24 Kelly, T. R.; Schmidt, T. E. and Haggerty, J. G. (1972) A convenient preparation of methyl and ethyl glyoxylate, *Synthesis*, 544-545.
25 hftp://www.accelrys.com/suppor/life/discover/forcefield/esffSBL.html
26 Soubrier, F.; Alhenc-Gelas, F.; Hubert, C.; Allegrini, J.; John, M.; Tregear, G. and Corvol, P. (1988) Two putative active centers in human angiotensin I-converting enzyme revealed by molecular cloning, *Proc. Natl. Acad. Sci. U.S.A.* 85, 9386-9390.
27 Georgiadis, D.; Cuniasse, P.; Cotton, J.; Yiotakis, A. and Dive, V. (2004) Structural determinants of RXPA380, a potent and highly selective inhibitor of the angiotensin-converting enzyme C-domain, *Biochemistry*, 43, 8048-8054.
28 Bersanetti, P. A.; Andrade, M. C. C; Casarini, D. E.; Juliano, M. A.; Nchinda, A. T.; Sturrock, E. D.; Juliano, L. and Carmona, A. K. (2004) Positional-scanning combinatorial libraries of fluorescence resonance energy transfer (FRET) peptides to define substrate specificity of angiotensin I-converting enzyme and development of selective C-domain substrates, *Biochemistry, accepted in press*.
29 Bala, M.; Pasha, M. A. Q.; Bhardwaj, D. K. and Pasha, S. (2002) Novel Peptidomimics as Angiotensin-Converting Enzymes inhibitors: A combinatorial approach, *Bioorg. and Med. Chem.*, 10, 3685-3691.
30 Da, C.-S.; Han, Z.-J.; Ni, M.; Yang, F.; Liu, D.-X.; Zhou, Y.-F. and Wang, R. (2003) A convenient synthesis of piperidine-based β-amino alcohols from L-Phe and highly enantioselective addition of diethyl zinc to aldehydes, *Tetrahedron: Asymmetry*, 14, 659-665.
31 (a) Hvidt, T. and Szarek, W. A. (1988) Synthesis of enantiomerically pure β-amino-α-methylene-γ-butyrolactones by way of ozonolysis of aromatic α-amino acids, *Can. J. Chem.*, 66(4), 779-782;
(b) Peng, S. and Winterfeldt, E. (1990) Enantiomerically pure indoloquinolizines from tryptophane, *Liebigs Ann. Chem.*, 313-318.
32 Borghi, C. and Ambrosioni E. (2003) Double-blind comparison between zofenopril and lisinopril in patients with acute myocardial infarction: Results of the survival of myocardial infarction long-term evaluation-2 (SMILE-2) study, *Am. Heart J.* 145, 80-87 and Buikema, H. (2003) Angiotensin-converting enzyme inhibitors zofenopril and lisinopril are both safe in the treatment of acute myocardial infarction, *Evidence-base Cardiov. Med.* 7, 131-132.
33 Cushman, D. W.; Cheung, H. S.; Sbo, E. F. and Ondetti, M. A. (1977) Design of potent competitive inhibitors of angiotensin-converting enzyme. Carboxyalkanoyl and mercaptoalkanoyl amino acids, *Biochemistry*, 16, 5484-5491.
34 Ondetti, M. A.; Rubin, B. and Cushman, D. W. (1977) Design of specific inhibitors of angiotensin-converting enzyme: New class of orally active antihypertensive agents, *Science*, 196, 441-444.
35 Brown, N. J. and Vaughan, D. E. (1998) Angiotensin-converting enzyme inhibitors, *Circulation*, 97(14), 1411-1420.
36 Georgíadis, D.; Cuniasse, P.; Cotton, J.; Yiotakis, A. and Dive, V. (2004) Structural determinants of RXPA380, a potent and highly selective inhibitor of the angiotensin-converting enzyme C-domain, *Biochemistry*, 43, 8048-8054.
37 Schnorrenberg, G.; Roos, O.; Losel, W.; Weidemann, I.; Gaida, W.; Hoefke, W.; Arndts, D. and Streller, I. (1989) Amino acid derivatives and their pharmaceutical use. In *USPTO Patent Full text and Image Database*, Boehringer Ingelheim GmbH; US, pp. 1-18.
38 (a) Hvidt, T. and Szarek, W. A. (1988) Synthesis of enantiomerically pure β-amino-α-methylene-γ-butyrolactones by way of ozonolysis of aromatic α-amino acids, *Can. J. Chem.*, 66(4), 779-782;
(b) Peng, S. and Winterfeldt, E. (1990) Enantiomerically pure indoloquinolizines from tryptophane, *Liebigs Ann. Chem.*, 313-318.

The invention claimed is:

1. A peptidomimetic having the sequence $N^2$—(R,S)-(1-Carbonyl-3-phenylpropyl)]-L-lysyl-L-tryptophan hydrochloride.

2. A composition comprising $N^2$—(R,S)-(1-Carbonyl-3-phenylpropyl)R-lysyl-L-tryptophan hydrochloride for treating hypertension and/or cardiovascular disease.

3. A method for treating hypertension, heart failure, myocardial infarction, and/or hypertensive and diabetic nephropathy comprising administering to a patient in need thereof an effective amount of $N^2$—(R,S)-(1-Carbonyl-3-phenylpropyl)]-L-lysyl-L-tryptophan hydrochloride.

* * * * *